(12) United States Patent
Sjostrom et al.

(10) Patent No.: US 8,708,891 B2
(45) Date of Patent: Apr. 29, 2014

(54) STEREOSCOPIC COUPLER FOR MECHANICALLY AND OPTICALLY COUPLING A STEREO ENDOSCOPE TO A STEREO ENDOSCOPIC CAMERA

(75) Inventors: Douglas Sjostrom, Tewksbury, MA (US); John E. Kennedy, Lowell, MA (US); Dennis Arsenault, Ashland, MA (US); Yuri Kazakevich, Newton, MA (US)

(73) Assignee: Viking Systems, Inc., Westborough, MA (US)

( * ) Notice: Subject to any disclaimer, the term of this patent is extended or adjusted under 35 U.S.C. 154(b) by 53 days.

(21) Appl. No.: 13/096,287

(22) Filed: Apr. 28, 2011

(65) Prior Publication Data
US 2011/0295071 A1 Dec. 1, 2011

Related U.S. Application Data (60) Provisional application No. 61/328,776, filed on Apr. 28, 2010.

(51) Int. Cl.
*A61B 1/04* (2006.01)
*A61B 1/00* (2006.01)
(52) U.S. Cl.
CPC ......... *A61B 1/00193* (2013.01); *A61B 1/00105* (2013.01); *A61B 1/00128* (2013.01)
USPC ............................. 600/111; 600/112; 600/167
(58) Field of Classification Search
USPC .................. 600/111, 112, 166, 167; 359/378; 348/45
See application file for complete search history.

(56) References Cited

U.S. PATENT DOCUMENTS

| | | | | |
|---|---|---|---|---|
| 4,340,811 A | * | 7/1982 | Yamashita et al. | 250/201.4 |
| 4,364,629 A | * | 12/1982 | Lang et al. | 359/377 |
| 4,611,888 A | | 9/1986 | Prenovitz et al. | |
| 4,697,894 A | * | 10/1987 | Takamura et al. | 359/503 |
| 4,844,071 A | * | 7/1989 | Chen et al. | 600/112 |
| 4,969,450 A | * | 11/1990 | Chinnock et al. | 600/109 |
| 5,122,650 A | | 6/1992 | McKinley | |
| 5,191,203 A | | 3/1993 | McKinley | |
| 5,222,482 A | * | 6/1993 | Clark | 600/111 |
| 5,355,253 A | * | 10/1994 | Nanjo et al. | 359/473 |
| 5,496,261 A | * | 3/1996 | Sander | 600/163 |
| 5,577,991 A | * | 11/1996 | Akui et al. | 600/111 |
| 5,647,838 A | | 7/1997 | Bloomer | |
| 5,673,147 A | | 9/1997 | McKinley | |
| 5,702,350 A | * | 12/1997 | Vry et al. | 600/166 |
| 5,743,847 A | * | 4/1998 | Nakamura et al. | 600/166 |
| 5,751,341 A | | 5/1998 | Chaleki et al. | |
| 5,776,049 A | * | 7/1998 | Takahashi | 600/111 |
| 5,860,912 A | * | 1/1999 | Chiba | 600/111 |
| 5,876,327 A | * | 3/1999 | Tsuyuki et al. | 600/112 |
| 6,113,533 A | * | 9/2000 | Howes et al. | 600/112 |
| 6,155,973 A | * | 12/2000 | Howes et al. | 600/112 |
| 6,219,182 B1 | | 4/2001 | McKinley | |
| 6,317,260 B1 | * | 11/2001 | Ito | 359/377 |

(Continued)

*Primary Examiner* — John P Leubecker
(74) *Attorney, Agent, or Firm* — Pandiscio & Pandiscio (57) ABSTRACT

A stereoscopic coupler for mechanically and optically coupling an endoscope to a portion of a camera, the stereoscopic coupler including means for mechanically and optically coupling the stereoscopic coupler to an endoscope; and means for mechanically and optically coupling the stereoscopic coupler to a portion of a camera; wherein the stereoscopic coupler includes a pair of optics; a mechanical actuator for operation by a user; and means for physically moving the pair of optics as a unit in response to movement of the mechanical actuator by the user.

23 Claims, 9 Drawing Sheets

(56) References Cited

U.S. PATENT DOCUMENTS

| | | |
|---|---|---|
| 6,898,022 B2 * | 5/2005 | Igarashi ........................ 359/676 |
| 7,671,888 B2 * | 3/2010 | Nogami et al. ................. 348/45 |
| 2002/0035310 A1 * | 3/2002 | Akui et al. .................... 600/111 |
| 2003/0083551 A1 * | 5/2003 | Takahashi ..................... 600/166 |
| 2004/0147809 A1 * | 7/2004 | Kazakevich ................... 600/178 |
| 2007/0010707 A1 * | 1/2007 | Leiner et al. .................. 600/112 |
| 2010/0238326 A1 * | 9/2010 | Luber ......................... 348/240.3 |

* cited by examiner

STEREOSCOPIC COUPLER FOR MECHANICALLY AND OPTICALLY COUPLING A STEREO ENDOSCOPE TO A STEREO ENDOSCOPIC CAMERA

REFERENCE TO PENDING PRIOR PATENT APPLICATION

This patent application claims benefit of prior U.S. Provisional Patent Application Ser. No. 61/328,776, filed Apr. 28, 2010 by Douglas Sjostrom et al. for OPTICAL ADAPTER FOR STEREO ENDOSCOPIC CAMERA, which patent application is hereby incorporated herein by reference.

FIELD OF THE INVENTION

This invention relates to visualization systems in general, and more particularly to stereoscopic visualization systems.

BACKGROUND OF THE INVENTION

A typical stereo endoscopic camera comprises two image sensors (e.g., CCD or CMOS sensors). The image sensors may be of a single-chip construction, or they may comprise 3-chip sensor blocks that include 3 sensors attached to a color-separating prism. The image sensors receive optical images generated by a stereo endoscope. Typically an opto-mechanical adapter (i.e., a stereoscopic coupler) is disposed between the stereo endoscope and the stereo endoscopic camera. The stereoscopic coupler generally serves three purposes: (i) it provides a secure mechanical locking mechanism between the stereo endoscope and the stereo endoscopic camera; (ii) it houses coupling optics for projecting the images from the stereo endoscope on the two image sensors of the stereo endoscopic camera; and (iii) it provides the focusing means for the coupling optics housed by the stereoscopic coupler.

Opto-mechanical adapters for non-stereo endoscopes and cameras are commonly available products in the industry and are well known to those skilled in the art.

Stereo endoscopes differ from their non-stereo counterparts in that they are more sensitive to optical misalignments. Not only must each channel of the stereo endoscope be properly optically aligned with the image sensors of the stereo endoscopic camera for the best image, but also key optical parameters for each channel (e.g., magnification, boresight, image rotation, image focus, etc.) must be identical between the two channels or an unwanted parallax will be created in the system, causing depth distortions and user strain/fatigue associated with converging the two images.

Prior art stereoscopic couplers all suffer from one or more deficiencies, including complexity of design, difficulties in maintaining optical alignment, cost of manufacture and maintenance, etc.

Thus there is a need for a new and improved stereoscopic coupler for mechanically and optically coupling a stereo endoscope to a stereo endoscopic camera.

SUMMARY OF THE INVENTION

The present invention provides a new and improved stereoscopic coupler for mechanically and optically coupling a stereo endoscope to a stereo endoscopic camera. This new and improved stereoscopic coupler provides precision alignment between the optics of the stereo endoscope and the optics of the stereo endoscopic camera, and provides an easy-to-use locking mechanism to secure the stereo endoscope to the stereo endoscopic camera.

In one preferred form of the invention, there is provided a stereoscopic coupler for mechanically and optically coupling an endoscope to a portion of a camera, the stereoscopic coupler comprising:

means for mechanically and optically coupling the stereoscopic coupler to an endoscope; and means for mechanically and optically coupling the stereoscopic coupler to a portion of a camera;

wherein the stereoscopic coupler comprises:

a pair of optics;

a mechanical actuator for operation by a user; and means for physically moving the pair of optics as a unit in response to movement of the mechanical actuator by the user.

In another preferred form of the invention, there is provided a stereoscopic coupler for mechanically and optically connecting an endoscope to a portion of a camera, the stereoscopic coupler comprising:

means for mechanically and optically coupling the stereoscopic coupler to an endoscope; and means for mechanically and optically coupling the stereoscopic coupler to a portion of a camera;

wherein the stereoscopic coupler comprises:

an element for ensuring axial alignment between an endoscope and the stereoscopic coupler;

an element for ensuring horizontal alignment between an endoscope and the stereoscopic coupler; and a releasable element for releasably securing an endoscope to the stereoscopic coupler.

In another preferred form of the invention, there is provided a stereoscopic coupler for mechanically and optically coupling an endoscope to a portion of a camera, the stereoscopic coupler comprising:

means for mechanically and optically coupling the stereoscopic coupler to an endoscope; and means for mechanically and optically coupling the stereoscopic coupler to a portion of a camera;

wherein the stereoscopic coupler comprises:

optics;

a mechanical actuator for operation by a user; and means for physically moving the optics as a unit in response to movement of the mechanical actuator by the user.

In another preferred form of the invention, there is provided a method for mechanically and optically coupling a stereo endoscope to a stereo endoscopic camera, the method comprising:

providing a stereoscopic coupler for mechanically and optically coupling an endoscope to a portion of a camera, the stereoscopic coupler comprising:

means for mechanically and optically coupling the stereoscopic coupler to an endoscope; and     means for mechanically and optically coupling the stereoscopic coupler to a portion of a camera;

wherein the stereoscopic coupler comprises:

a pair of optics;

a mechanical actuator for operation by a user; and means for physically moving the pair of optics as a unit in response to movement of the mechanical actuator by the user;

mounting the stereoscopic coupler to the stereo endoscopic camera; and mounting the stereo endoscope to the stereoscopic coupler.

In another preferred form of the invention, there is provided a method for mechanically and optically coupling a stereo endoscope to a stereo endoscopic camera, the method comprising:

providing a stereoscopic coupler for mechanically and optically connecting an endoscope to a portion of a camera, the stereoscopic coupler comprising:

means for mechanically and optically coupling the stereoscopic coupler to an endoscope; and means for mechanically and optically coupling the stereoscopic coupler to a portion of a camera;

wherein the stereoscopic coupler comprises:

an element for ensuring axial alignment between an endoscope and the stereoscopic coupler;

an element for ensuring horizontal alignment between an endoscope and the stereoscopic coupler; and a releasable element for releasably securing an endoscope to the stereoscopic coupler;

mounting the stereoscopic coupler to the stereo endoscopic camera; and mounting the stereo endoscope to the stereoscopic coupler.

In another preferred form of the invention, there is provided a method for mechanically and optically coupling a stereo endoscope to a stereo endoscopic camera, the method comprising:

providing a stereoscopic coupler for mechanically and optically coupling an endoscope to a portion of a camera, the stereoscopic coupler comprising:

means for mechanically and optically coupling the stereoscopic coupler to an endoscope; and means for mechanically and optically coupling the stereoscopic coupler to a portion of a camera;

wherein the stereoscopic coupler comprises:

optics;

a mechanical actuator for operation by a user; and means for physically moving the optics as a unit in response to movement of the mechanical actuator by the user;

mounting the stereoscopic coupler to the stereo endoscopic camera; and mounting the stereo endoscope to the stereoscopic coupler.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
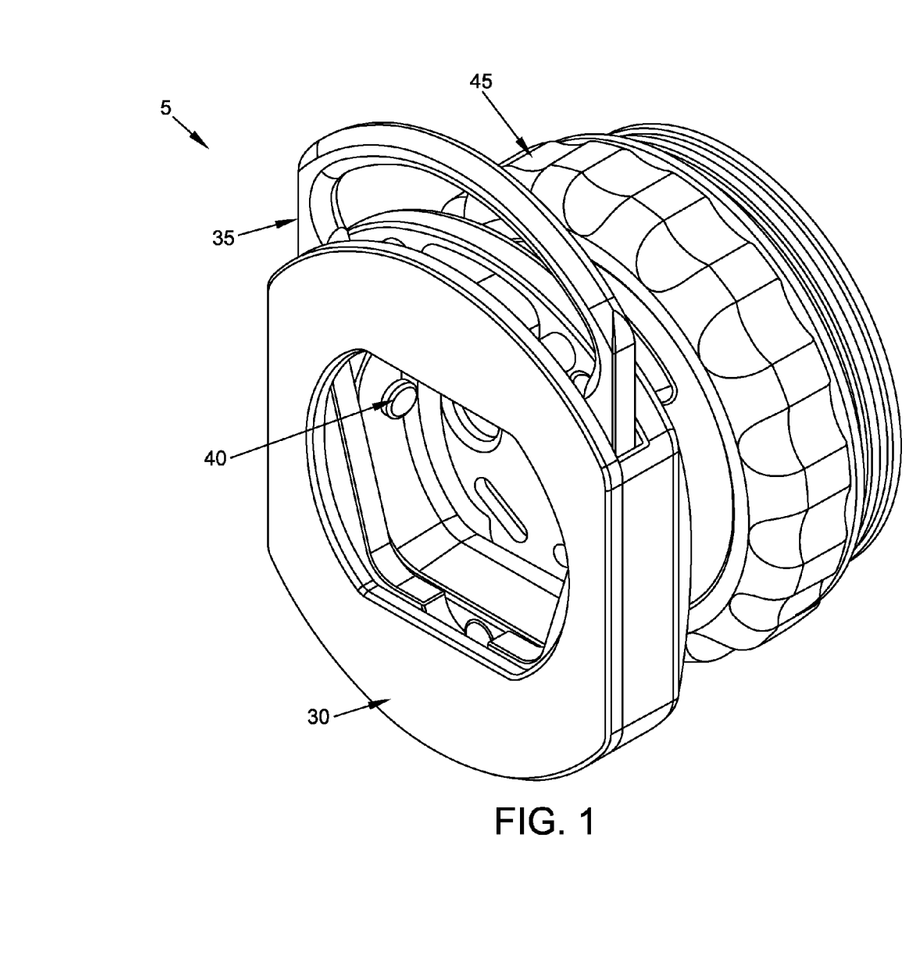
FIG. 1 is a schematic distal-end view showing a novel stereoscopic coupler formed in accordance with the present invention.
Figure 2:
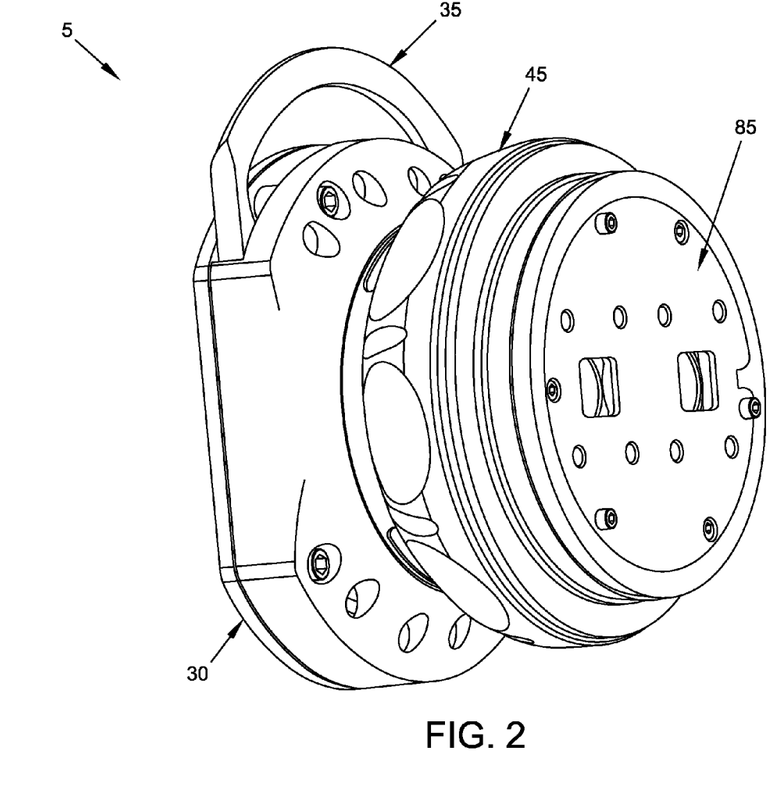
FIG. 2 is a schematic proximal-end view of the stereoscopic coupler shown in FIG. 1.
Figure 3:
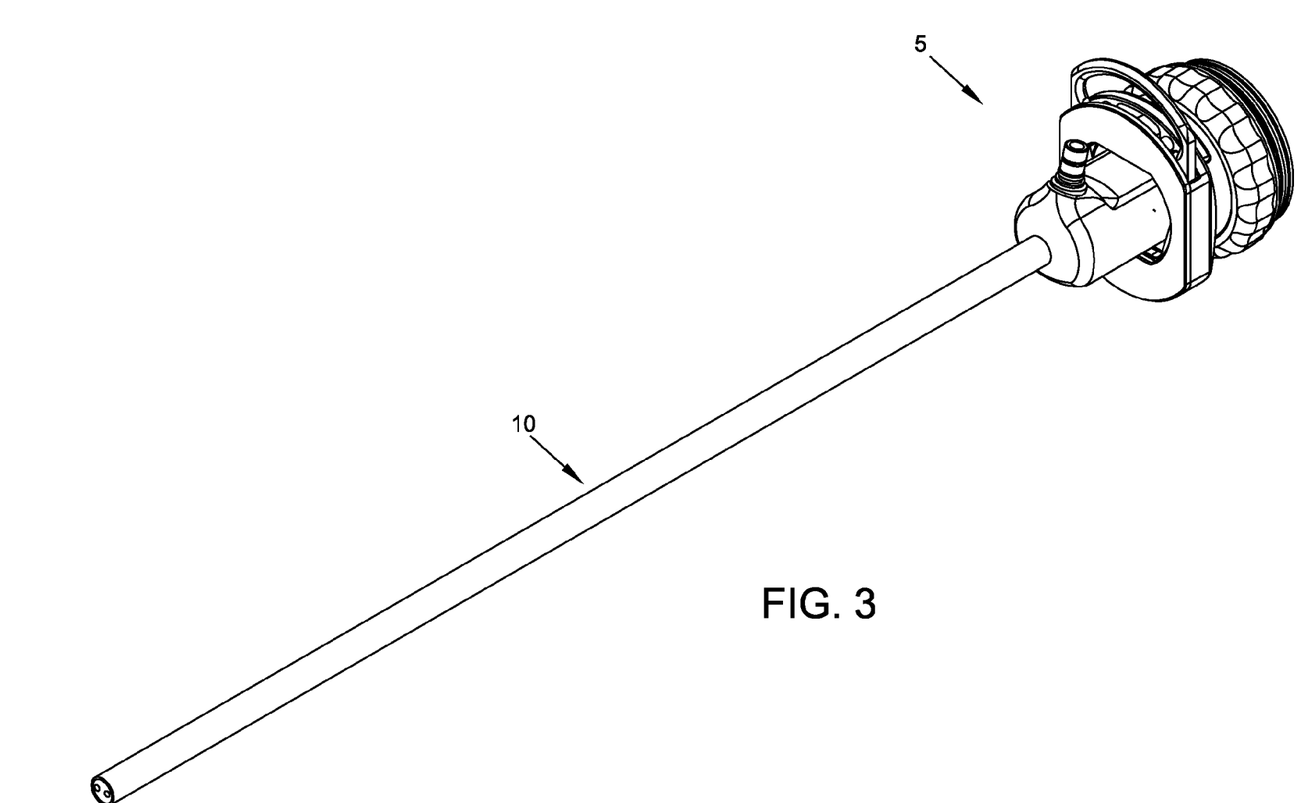
FIG. 3 is a schematic view showing a stereo endoscope connected to the stereoscopic coupler shown in FIG. 1.
Figure 4:
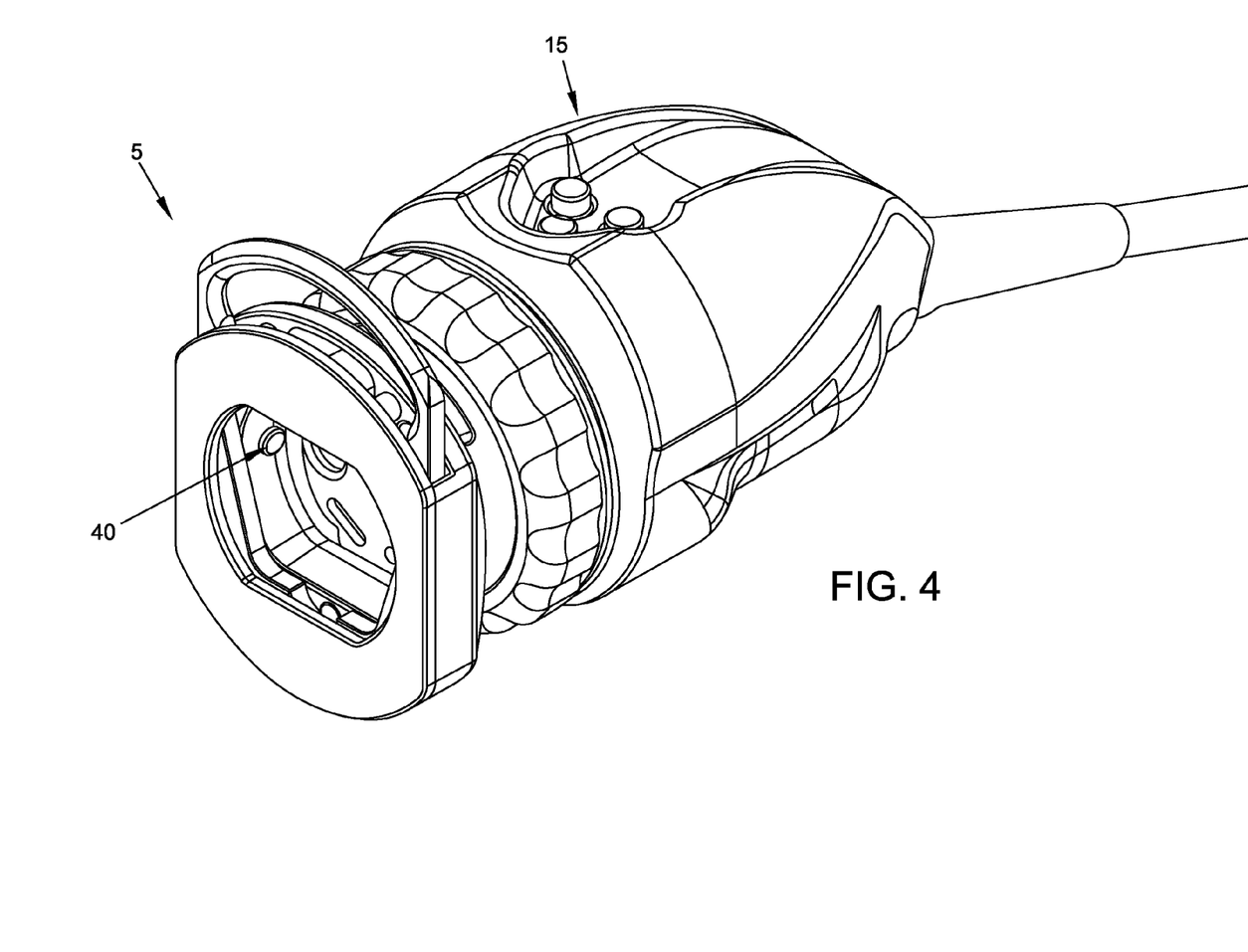
FIG. 4 is a schematic view showing the stereoscopic coupler of FIG. 1 connected to a stereo endoscopic camera.

Looking first at FIGS. 1 and 2, there is shown a novel stereoscopic coupler 5 for mechanically and optically coupling a stereo endoscope to a stereo endoscopic camera. FIGS. 3 and 4 show stereoscopic coupler 5 secured to a stereo endoscope 10 (FIG. 3) and stereoscopic coupler 5 secured to a stereo endoscopic camera 15 (FIG. 4.).

Figure 5:
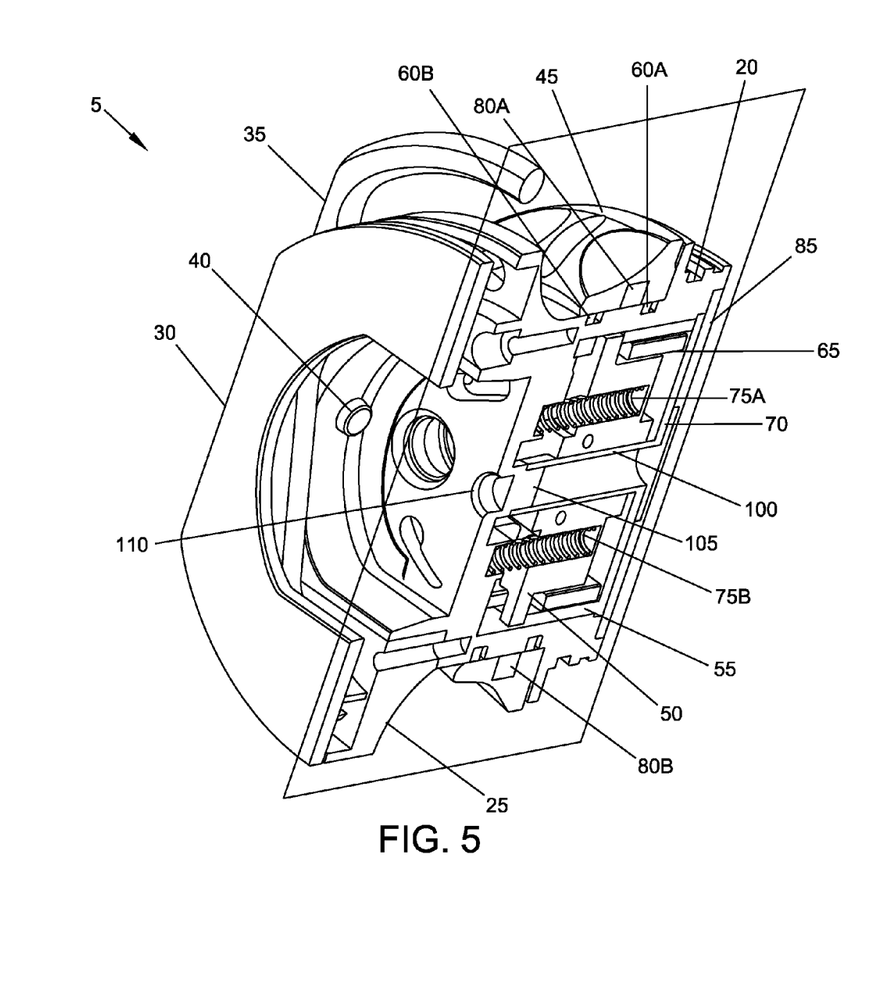
FIGS. 5 and 6 are schematic sectional views showing various components of the stereoscopic coupler shown in FIG. 1.
Figure 6:
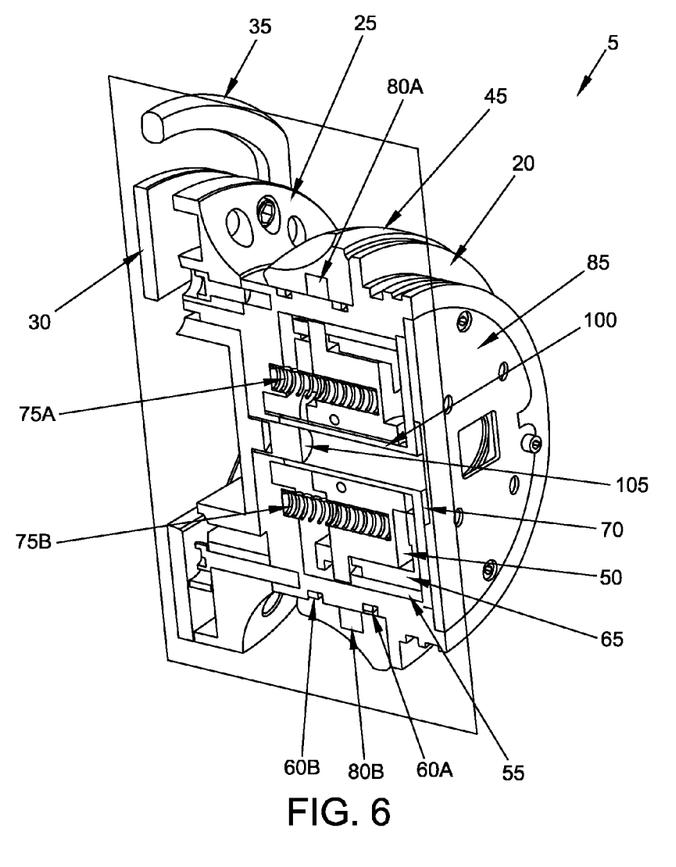
Figure 7:
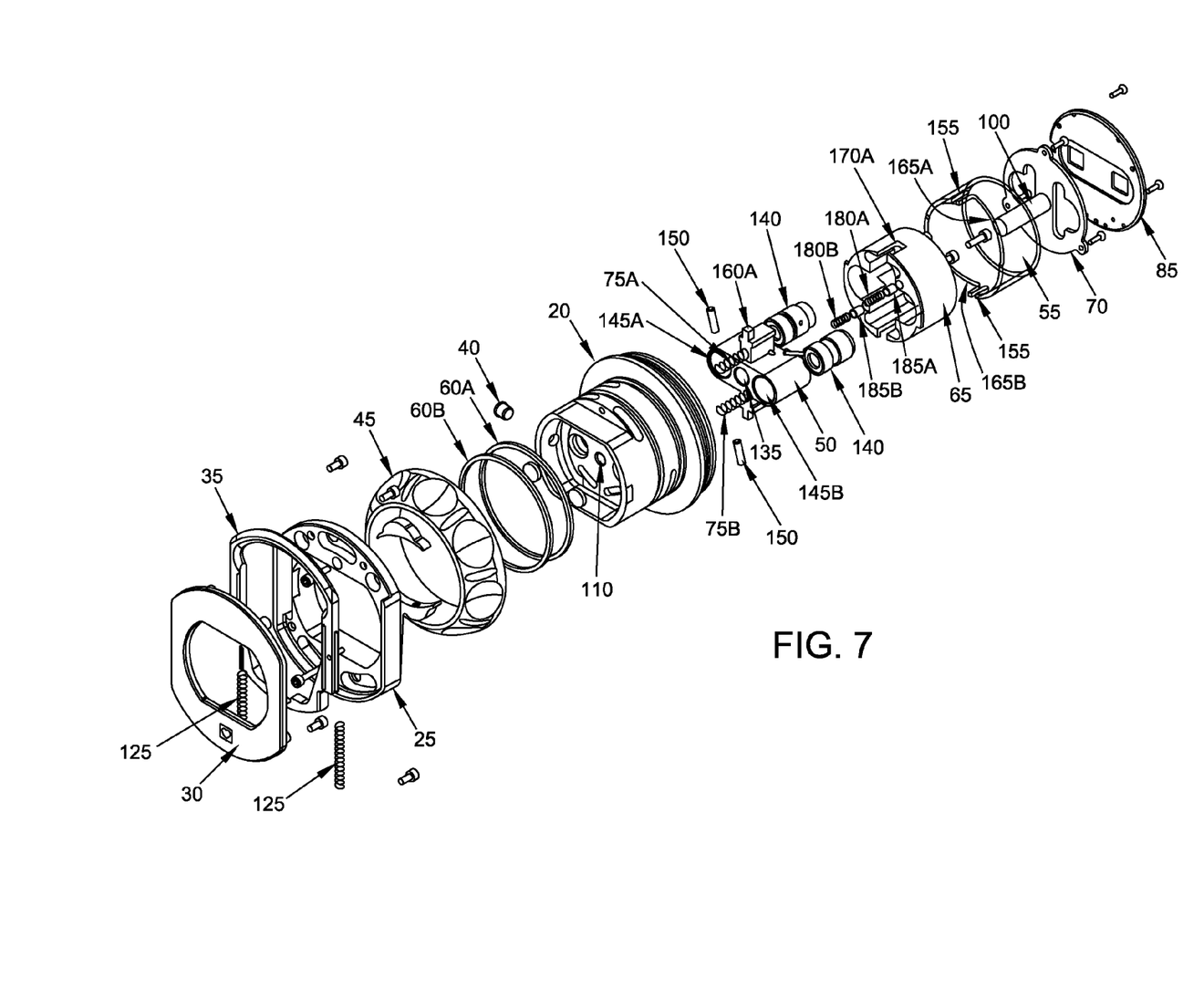
FIG. 7 is a schematic exploded view showing various components of the stereoscopic coupler shown in FIG. 1.

Functionally, and looking next at FIGS. 5-7, stereoscopic coupler 5 may be considered to constitute three main sections, each providing a different function and serving a different purpose:

(i) a "scope locking" section situated distally on stereoscopic coupler 5 and comprising the distal portion of the main housing 20, front flange 25, front cover 30, a bail 35 and a radial locating pin 40;

(ii) a "focusing mechanism" section situated primarily in the middle of the stereoscopic coupler and comprising the middle portion of the main housing 20, focusing ring 45, binocular cell housing 50, cam ring 55, elastomeric seals 60A, 60B, load ring 65, clutch plate 70, return springs 75A, 75B, and cam pin sockets 80A, 80B; and (iii) a "camera attachment" section situated proximally on stereoscopic coupler 5 and comprising the proximal portion of the main housing 20 and a sensor mounting plate 85 which is mounted to the image sensor (not shown) of stereo endoscopic camera 15.

The following is the description of some of the distinct features and operational principles of stereoscopic coupler 5.

The "Scope Locking" Section

Figure 8:
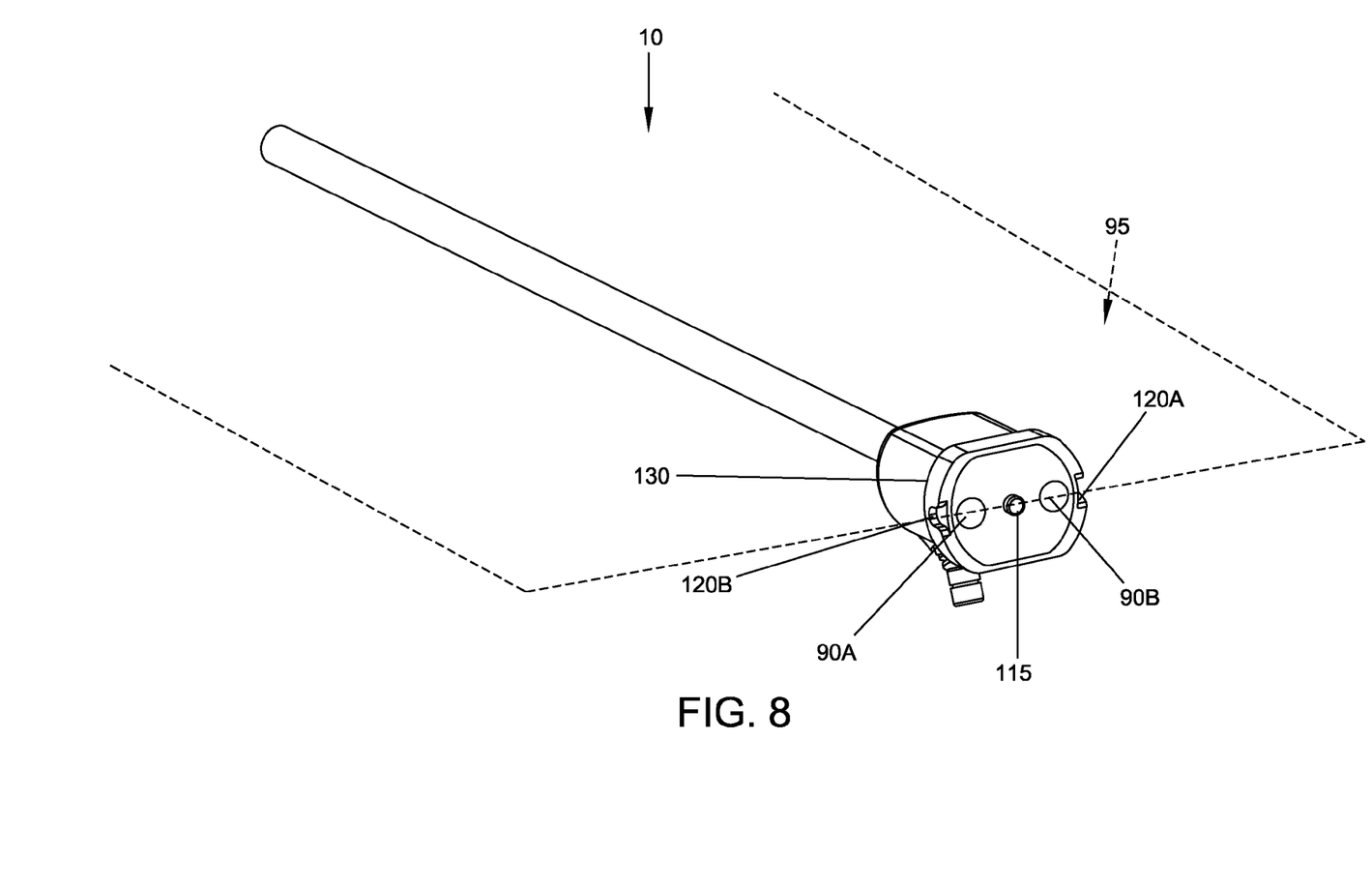
FIG. 8 is a schematic view showing various aspects of the stereo endoscope shown in FIG. 3.

The "scope locking" section receives, aligns and securely locks in place a stereo endoscope (e.g., the stereo endoscope 10 shown in FIGS. 3 and 8). Stereo endoscope 10 typically has two optical channels 90A, 90B (FIG. 8) separated by a predetermined distance. The theoretical plane passing through the optical axes of the two optical channels 90A, 90B defines the horizontal plane 95 of the system. For proper performance of the stereo endoscopic system, two alignments are essential: (a) the axial alignment of each optical channel 90A, 90B of the stereo endoscope 10 with its corresponding optical channel of the stereo endoscopic camera 10, and (b) the horizontal alignment of the endoscope horizontal plane 95 with the corresponding horizontal plane of the stereo endoscopic camera 10.

The present invention provides highly precise axial and horizontal alignment of the coupling optics of the stereoscopic coupler with respect to the endoscope optics.

As shown in FIGS. 5-7, the clutch plate 70 has a hollow central shaft 100 fabricated by precision machining and a centerless grinding technique known to those skilled in the art. The distal portion of main housing 20 has a cylindrical protrusion 105 that fits into hollow shaft 100 of clutch plate 70, thereby axially locating main housing 20 relative to clutch plate 70. On its distal side, main housing 20 has a central blind hole 110 that receives the corresponding central pin 115 (FIG. 8) of stereo endoscope 10. Thus, stereo endoscope 10 is precisely axially aligned with hollow shaft 100 of clutch plate 70.

Horizontal alignment of stereo endoscope 10 is achieved by radial locating pin 40 and corresponding grooves 120A, 120B (FIG. 8) formed in the proximal portion of stereo endoscope 10.

Figure 9:
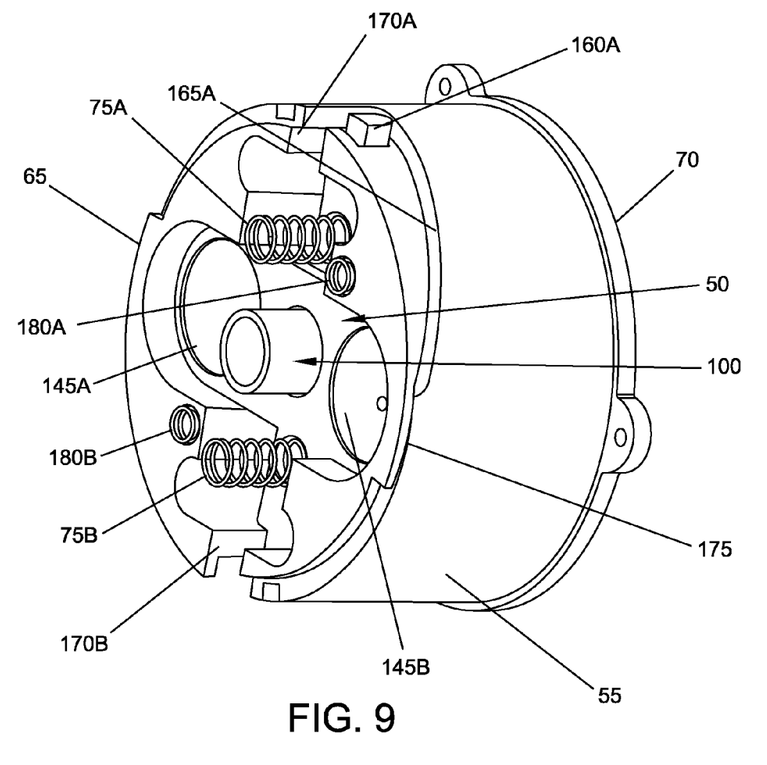
FIG. 9 is a schematic view showing selected additional aspects of stereoscopic coupler shown in FIG. 1.

Stereo endoscope 10 is detachably connected to stereoscopic coupler 5 (FIG. 3) by means of the scope locking section. More particularly, in order to attach stereo endoscope 10 to stereoscopic coupler 5, the adapter's spring-loaded bail 35 is depressed against the force of springs 125 so as to open up the entire distal cavity of main housing 20. Stereo endoscope 10 is then inserted into the distal end of stereoscopic coupler 5 in such a way that the endoscope's central pin 115 is received by blind hole 110 of main housing 20 of the stereoscopic coupler while one of the endoscope's peripheral grooves 120A, 120B aligns with the radial locating pin 40 of the stereoscopic coupler. After full insertion of the proximal end of the stereo endoscope into the distal end of the stereoscopic coupler, the spring-loaded bail 35 is released so that the bail locks stereo endoscope 10 to stereoscopic coupler 5 by exerting force at the endoscope's proximal chamfered surface 130 (FIG. 8) towards main housing 20 of the stereoscopic coupler. It can also be seen from FIG. 5 that binocular cell housing 50 has a cylindrical central internal surface 135 riding on hollow central shaft 100 of clutch plate 70. This arrangement ensures precise axial alignment of the coupling optics 140 that are housed in the corresponding openings 145A and 145B of the binocular cell housing 50 (FIGS. 7 and 9).

It should be appreciated that the symmetry of the design with respect to the horizontal plane 95 allows for two possible attachments of stereo endoscope 10 to stereoscopic coupler 5, with 180° angular relations between each position, i.e., radial locating pin 40 may be received in either one of the peripheral grooves 120A, 120B of the stereo endoscope.

It should also be appreciated that, if desired, two radial locating pins 40 may be provided on the distal portion of main housing 20, with the two radial locating pins 40 being diametrically opposed across the diameter of main housing 20, so that one radial locating pin 40 may be received in the endoscope's peripheral groove 120A and the other radial locating pin 40 may be received in the endoscope's peripheral groove 120B. Again, even where two radial locating pins 40 are provided, the symmetry of the design allows for two possible attachments of stereo endoscope 10 to stereo coupler 5, with 180° angular rotation between each position, i.e., one radial locating pin 40 may be received one of the peripheral grooves 120A, 120B of the stereo endoscope and the other radial locating pin 40 may be received in the other of the peripheral grooves 120A, 120B of the stereo endoscope.

The "Focusing Mechanism" Section

FIGS. 5-7 and 9 show details of the focusing mechanism section of stereoscopic coupler 5 (in FIG. 9, main housing 20 has been removed for clarity). When focusing ring 45 is rotated, cam ring 55 turns with it as a unit. The rigid connection between focusing ring 45 and cam ring 55 is provided by cam pins 150 which extend between cam pin seats 155 on cam ring 55 and cam pin sockets 80A and 80B (see FIG. 5) in focusing ring 45. The protruding fingers 160A and 160B of binocular cell housing 50 are pressed to the cam surfaces 165A, 165B of cam ring 55 by the springs 75A and 75B. Rotation of cell housing 50 is prevented by precisely machined grooves 170A and 170B of load ring 65. As the cam ring 55 turns clockwise and counterclockwise in response to counterpart rotation of focusing ring 45 by the user, binocular cell housing 50 moves axially in proximal and distal directions, respectively, whereby to move coupling optics 140 axially, in a coupled manner, in proximal and distal directions, respectively.

Thus, it will be seen that, in view of the foregoing construction, when focusing ring 45 is rotated about its axis, cam ring 55 rotates correspondingly and causes, via camming action, axial movement of binocular cell housing 50, and therefore axial movement of coupling optics 140, within stereoscopic coupler 5. Significantly, coupling optics 140 move in conjunction with one another in a coupled manner.

The present invention also allows for adjustment of the amount of torque required for rotation of focusing ring 45. This is done by adjusting the amount of friction force created between load ring 65 and cam ring 55. As can be seen in FIG. 9, while cam ring 55 rotates, it maintains a certain surface contact with load ring 65 (shown in FIG. 9 by numeral 175). The friction force between load ring 65 and cam ring 55 impacts the torque of focusing ring 45. The friction force is determined by the axial force created between the two parts that is applied by compression springs 180A and 180B. The compression of these springs 180A, 180B is adjustable via threaded plungers 185A, 185B situated at the proximal ends of springs 180A, 180B (FIG. 7).

The "Camera Attachment" Section

Stereoscopic coupler 5 may be permanently or detachably connected to stereo endoscopic camera 15. Appropriate sealing means well known in the art (e.g., O-rings, bal-seals, quad-rings, plastic gaskets and the like) are provided between the stereoscopic coupler and the stereo endoscopic camera so as to ensure a hermetically-sealed assembly.

The above description outlines the preferred embodiments of the invention. Other embodiments are also possible within the framework of the invention. For instance, in the preferred embodiment, the binocular cell housing 50 is moved axially by cam ring 55. Alternatively, axial motion of binocular cell housing 50 may be effected by a lead screw rigidly connected to the focus ring. In this case, binocular cell housing 50 would have a corresponding threaded central hole. Still other means for effecting axial motion of binocular cell housing 50 will be apparent to those skilled in the art in view of the present disclosure.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A stereoscopic coupler for mechanically and optically coupling a stereoscopic endoscope having a left optical channel and a right optical channel to a portion of a stereoscopic camera having a left optical channel and a right optical channel so that the left optical channel of the stereoscopic endoscope optically communicates with the left optical channel of the stereoscopic camera and the right optical channel of the stereoscopic endoscope optically communicates with the right optical channel of the stereos camera, the stereoscopic coupler comprising:

means for mechanically and optically coupling the stereoscopic coupler to a stereoscopic endoscope; and means for mechanically and optically coupling the stereoscopic coupler to a portion of a stereoscopic camera;

wherein the stereoscopic coupler comprises:

a left optical channel comprising left optics;

a right optical channel comprising right optics;

a mechanical actuator for operation by a user; and
means for physically moving the left optics of the left optical channel and the right optics of the right optical channel as a single unit in response to movement of the mechanical actuator by the user;

wherein the means for mechanically and optically coupling the stereoscopic coupler to a stereoscopic endoscope comprise:
an element for ensuring axial alignment between the left optical channel of the stereoscopic endoscope and the left optical channel of the stereoscopic coupler and for ensuring axial alignment between the right optical channel of the stereoscopic endoscope and the right optical channel of the stereoscopic coupler;
an element for ensuring horizontal alignment between the left optical channel of the stereoscopic endoscope and the left optical channel of the stereoscopic coupler and for ensuring horizontal alignment between the right optical channel of the stereoscopic endoscope and the right optical channel of the stereoscopic coupler; and
a releasable element for releasably securing the stereoscopic endoscope to the stereoscopic coupler so as to allow for rapid engagement and disengagement of the stereoscopic endoscope with the stereoscopic coupler.

2. A stereoscopic coupler according to claim 1 wherein the mechanical actuator comprises a focusing ring.

3. A stereoscopic coupler according to claim 2 wherein the left optical channel and the right optical channel are disposed about a longitudinal axis, and further wherein the focusing ring is disposed coaxially about the longitudinal axis.

4. A stereoscopic coupler according to claim 2 wherein the means for moving the left and right optics as a single is configured to transfer circumferential movement of the focusing ring to longitudinal movement of the left and right optics.

5. A stereoscopic coupler according to claim 4 wherein the means for moving the left and right optics as a single unit comprises a cam and a cam follower.

6. A stereoscopic coupler according to claim 5 wherein the left and right optics are mounted to a carriage, and further wherein one of the cam and cam follower is connected to the carriage and the other of the cam and cam follower is connected to the focusing ring.

7. A stereoscopic coupler according to claim 6 further comprising means for adjusting the amount of torque required to rotate the focusing ring.

8. A stereoscopic coupler according to claim 7 wherein the cam is carried by a cam ring which is secured to the focusing ring, wherein the cam follower is carried by the carriage which is disposed within a load ring so that the carriage is longitudinally movable relative to the load ring but rotationally fixed relative to the load ring, and further wherein the means for adjusting the amount of torque required to rotate the focusing ring comprises an adjustable spring for forcing the load ring against the cam ring.

9. A stereoscopic coupler according to claim 8 wherein the adjustable spring comprises a compression spring which is adjusted via a threaded plunger.

10. A stereoscopic coupler according to claim 1 wherein the stereoscopic coupler is formed independently of the stereoscopic camera.

11. A stereoscopic coupler according to claim 1 wherein the stereoscopic coupler is formed integral with a portion of the stereoscopic camera.

12. A stereoscopic coupler according to claim 1 wherein the camera comprises a housing, and further wherein the stereoscopic coupler is formed integral with the housing of the stereoscopic camera.

13. A stereoscopic coupler according to claim 1 wherein the element for ensuring axial alignment comprises a recess for receiving a counterpart projection on a stereoscopic endoscope.

14. A stereoscopic coupler according to claim 1 wherein the element for ensuring axial alignment comprises a projection for receipt in a counterpart recess on a stereoscopic endoscope.

15. A stereoscopic coupler according to claim 1 wherein the element for ensuring horizontal alignment comprises a recess for receiving a counterpart projection on a stereoscopic endoscope.

16. A stereoscopic coupler according to claim 1 wherein the element for ensuring horizontal alignment comprises a projection for receipt in a counterpart recess on a stereoscopic endoscope.

17. A stereoscopic coupler according to claim 1 wherein the releasable element comprises a bail.

18. A stereoscopic coupler according to claim 1 wherein the stereoscopic coupler is formed independently of the stereoscopic endoscope.

19. A stereoscopic coupler according to claim 1 wherein the stereoscopic coupler is formed integral with a portion of the stereoscopic endoscope.

20. A method for mechanically and optically coupling a stereoscopic endoscope having a left optical channel and a right optical channel to a portion of a stereoscopic camera having a left optical channel and a right optical channel so that the left optical channel of the stereoscopic endoscope optically communicates with the left optical channel of the stereoscopic camera and the right optical channel of the stereoscopic endoscope optically communicates with the right optical channel of the stereoscopic camera, the method comprising:
providing a stereoscopic coupler for mechanically and optically coupling a stereoscopic endoscope to a portion of a stereoscopic camera, the stereoscopic coupler comprising:
means for mechanically and optically coupling the stereoscopic coupler to a stereoscopic endoscope; and
means for mechanically and optically coupling the stereoscopic coupler to a portion of a stereoscopic camera;
wherein the stereoscopic coupler comprises:
a left optical channel comprising left optics;
a right, optical channel comprising right optics;
a mechanical actuator for operation by a user; and
means for physically moving the left optics of the left optical channel and the right optics of the right optical channel as a single unit in response to movement of the mechanical actuator by the user;
wherein the means for mechanically and optically coupling the stereoscopic coupler to a stereoscopic endoscope comprise:
an element for ensuring axial alignment between the left optical channel of the stereoscopic endoscope and the left optical channel of the stereoscopic coupler and for ensuring axial alignment between the right optical channel of the stereoscopic endoscope and the right optical channel of the stereoscopic coupler;
an element for ensuring horizontal alignment between the left optical channel of the stereoscopic endoscope and the left optical channel of the stereoscopic coupler and for ensuring horizontal alignment between the right optical channel of the stereoscopic endoscope and the right optical channel of the stereoscopic coupler; and a releasable element for releasably securing the stereoscopic endoscope to the stereoscopic coupler so as to allow for rapid engagement and disengagement of the stereoscopic endoscope with the stereoscopic coupler;

mounting the stereoscopic coupler to the stereoscopic camera; and mounting the stereoscopic endoscope to the stereoscopic coupler.

21. A method according to claim 20 wherein the stereoscopic coupler is mounted to the stereoscopic camera during manufacture.

22. A stereoscopic coupler for mechanically and optically coupling an endoscope to a portion of a camera, the stereoscopic coupler comprising:

means for mechanically and optically coupling the stereoscopic coupler to an endoscope; and means for mechanically and optically coupling the stereoscopic coupler to a portion of a camera;

wherein the stereoscopic coupler comprises:

a pair of optics;

a mechanical actuator for operation by a user; and means for physically moving the pair of optics as a unit in response to movement of the mechanical actuator by the user;

wherein the mechanical actuator comprises a focusing ring;

wherein the means for moving the pair of optics is configured to transfer circumferential movement of the focusing ring to longitudinal movement of the pair of optics;

wherein the means for moving the pair of optics comprises a cam and a cam follower;

wherein the pair of optics are mounted to a carriage, and further wherein one of the cam and cam follower is connected to the carriage and the other of the cam and cam follower is connected to the focusing ring;

further comprising means for adjusting the amount of torque required to rotate the focusing ring;

wherein the cam is carried by a cam ring which is secured to the focusing ring, wherein the cam follower is carried by the carriage which is disposed within a load ring so that the carriage is longitudinally movable relative to the load ring but rotationally fixed relative to the load ring, and further wherein the means for adjusting the amount of torque required to rotate the focusing ring comprises an adjustable spring for forcing the load ring against the cam ring.

23. A stereoscopic coupler according to claim 22 wherein the adjustable spring comprises a compression spring which is adjusted via a threaded plunger.

* * * * *